(12) United States Patent
Dittmer

(10) Patent No.: US 9,410,948 B2
(45) Date of Patent: Aug. 9, 2016

(54) MANIPULATION OF MAGNETIC PARTICLES IN A BIOLOGICAL SAMPLE

(75) Inventor: Wendy U. Dittmer, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 168 days.

(21) Appl. No.: 13/258,200

(22) PCT Filed: Mar. 19, 2010

(86) PCT No.: PCT/IB2010/051206
§ 371 (c)(1),
(2), (4) Date: Sep. 22, 2011

(87) PCT Pub. No.: WO2010/109392
PCT Pub. Date: Sep. 30, 2010

(65) Prior Publication Data
US 2012/0014836 A1    Jan. 19, 2012

(30) Foreign Application Priority Data
Mar. 23, 2009 (EP) .................................... 09305253

(51) Int. Cl.
| G01N 33/00 | (2006.01) |
| B01D 21/00 | (2006.01) |
| B03C 1/02 | (2006.01) |
| B03C 1/30 | (2006.01) |
| B01D 35/06 | (2006.01) |
| G01R 33/12 | (2006.01) |
| G01N 33/543 | (2006.01) |
(Continued)

(52) U.S. Cl.
CPC ....... *G01N 33/54326* (2013.01); *B01L 2200/16* (2013.01); *B01L 2400/043* (2013.01); *G01N 27/72* (2013.01); *G01N 27/745* (2013.01); *G01N 33/54333* (2013.01); *G01R 33/12* (2013.01)

(58) Field of Classification Search
CPC .................. G01N 33/54326; G01N 33/54333; G01N 27/72; G01N 27/745; B01L 2200/16; B01L 2400/043; G01R 33/12
USPC ........... 422/68.1, 69, 502, 504, 507; 210/222, 210/695
See application file for complete search history.

(56) References Cited

U.S. PATENT DOCUMENTS

| 5,863,708 A | 1/1999 | Zanzucchi |
| 6,667,725 B1 | 12/2003 | Simons |
(Continued)

FOREIGN PATENT DOCUMENTS

| CN | 1624447 A | 6/2005 |
| CN | 101158697 A | 4/2008 |
(Continued)

OTHER PUBLICATIONS

Bruls, D.M. et al "Rapid Integrated Biosensor for Multiplexed Immunoassays based on Actuated Magnetic Nanoparticles" Lab on a Chip, vol. 9. No. 24. pp. 3504-3510. 2009.

*Primary Examiner* — Jennifer Wecker

(57) ABSTRACT

A microfluidic device, used with a processing device having a magnetic supplier, including a chamber arranged to receive a biological sample and at least one magnetic particle, and a storage for storing information comprising a magnetic protocol in a form readable by the processing device. The magnetic supplier is configured to generate magnetic forces on the magnetic particle(s) according to this magnetic protocol read from the storage.

20 Claims, 1 Drawing Sheet

(51) Int. Cl.
  *G01N 30/96* (2006.01)
  *B01L 3/00* (2006.01)
  *C12M 3/00* (2006.01)
  *G06F 17/00* (2006.01)
  *G01N 27/74* (2006.01)
  *G01N 27/72* (2006.01)

(56) References Cited

U.S. PATENT DOCUMENTS

| | | | |
|---|---|---|---|
| 7,416,700 B2 | 8/2008 | Buechler | |
| 8,217,647 B2* | 7/2012 | Dittmer | B82Y 25/00 324/260 |
| 2002/0039783 A1 | 4/2002 | McMillan | |
| 2002/0042125 A1 | 4/2002 | Petersen | |
| 2003/0003464 A1 | 1/2003 | Phan | |
| 2005/0013741 A1* | 1/2005 | a' Brassard | B03C 1/288 210/695 |
| 2005/0019213 A1* | 1/2005 | Kechagia et al. | 422/57 |
| 2005/0066246 A1 | 3/2005 | Maltseff | |
| 2006/0160205 A1 | 7/2006 | Blackburn | |
| 2007/0031819 A1 | 2/2007 | Koschwanez | |
| 2007/0114180 A1 | 5/2007 | Ramanathan | |
| 2007/0117214 A1* | 5/2007 | Masters et al. | 436/149 |
| 2007/0248497 A1* | 10/2007 | Robillot | 422/100 |
| 2008/0010520 A1 | 1/2008 | Bjerke | |
| 2008/0160634 A1* | 7/2008 | Su et al. | 436/501 |
| 2008/0162054 A1 | 7/2008 | Tam | |
| 2008/0246470 A1* | 10/2008 | Kahlman | B82Y 25/00 324/234 |
| 2009/0053827 A1* | 2/2009 | Taylor et al. | 436/501 |
| 2009/0170212 A1* | 7/2009 | Van Der Wijk | B82Y 25/00 436/149 |
| 2009/0317896 A1* | 12/2009 | Yoo | 435/287.1 |
| 2010/0015728 A1* | 1/2010 | Dilleen et al. | 436/536 |
| 2010/0194386 A1* | 8/2010 | Prins | G01N 33/54333 324/228 |

FOREIGN PATENT DOCUMENTS

| | | |
|---|---|---|
| CN | 101356429 A | 1/2009 |
| JP | 2004317363 A | 11/2004 |
| JP | 2007047110 A | 2/2007 |
| JP | 2009536348 A | 10/2009 |
| WO | 2004090503 A2 | 10/2004 |
| WO | 2007129275 A2 | 11/2007 |

* cited by examiner

MANIPULATION OF MAGNETIC PARTICLES IN A BIOLOGICAL SAMPLE

FIELD OF THE INVENTION

The present invention relates to a system arranged for and a method of magnetically manipulating magnetic particles contained in a biological sample. More especially, the invention comprises the appliance of at least one magnetic field generated by a magnetic supplier for generating magnetic field(s) (e.g. magnets and/or electromagnets) to the magnetic particles, when the biological sample is in a microfluidic device (e.g. a cartridge) to be used with a processing device comprising a magnetic supplier (e.g. permanent magnets and/or electromagnets). Typically, the magnetic supplier generates at least one magnetic field according to a predetermined magnetic protocol.

BACKGROUND OF THE INVENTION

This magnetic manipulation in a microfluidic device may be used for instance for mixing magnetic particles in the biological sample, for flowing magnetic particles according to a specific path in the microfluidic device or for actuating magnetic particles in view of a bonding with a sensing surface of the microfluidic device.

In latter case, the assembly of the microfluidic device and the processing device can be a biosensor if it further comprises a detector able to detect magnetic particles bound to the sensing surface. Such biosensors using magnetic particles are known for rapid and sensitive diagnostics and may be designed to detect biological targets labeled with these magnetic particles or with other types of labels (fluorescence, dyes, etc.) bound to the magnetic particles. The performance of a magnetic particle assay in the detection of a target molecule is highly dependent upon the magnetic protocol that is used by the magnetic supplier to control the motion of the particles during the assay.

Typically, the magnetic protocol is programmed into the processing device prior to performing the magnetic manipulation.

If one changes one or more of the above product characteristics (e.g. target molecule, assay type, assay condition, sample type and the like), it is preferable that the user is able to modify the magnetic protocol so as to maximize the sensitivity and/or accuracy of the measurements according to said changes of products characteristics.

Therefore the processing device could be provided with a user interface to perform this operation.

These modifications slow-down the use of the system or biosensor and a risk of error increases, which means a low ease-of-use and low fail-safe capabilities.

SUMMARY OF THE INVENTION

It is an object of the present invention to provide an improved method for performing a magnetic manipulation in a microfluidic system (i.e. comprising a microfluidic device and a processing device) taking into account the above mentioned problem.

It is a further object of the present invention to provide such a system easier to use, especially with a more simple user interface.

It is another object to speed-up the use of the system.

It is another object to improve the control of the magnetic manipulation of this system in view of increasing the sensitivity and accuracy of desired purpose to be reached when using this system (e.g. increasing the detection sensitivity if this system is a biosensor).

It is another object to decrease the cost of the system, and especially the cost of the processing device.

These and other objects are solved by the features of the independent claims. The dependent claims are directed to preferred embodiments of the present invention.

The present invention may be based on the idea to provide a link between a microfluidic device (or a cartridge or a cartridge assembly) to be used and a specific magnetic protocol optimized for said device and/or according to other parameters, such as use the system. The information regarding the magnetic protocol may either be provided directly in or on the cartridge or may come together with the cartridge on, e.g., a chip (e.g. sold together with the cartridge, in a same package). Thus, the magnetic protocol does not have to be programmed into the biosensor which speeds up the performance and eliminates mistakes.

As a first embodiment, the invention proposes a microfluidic device to be used with a processing device comprising a magnetic supplier (i.e. a generator of magnetic field(s) such as for example permanent magnets and/or electromagnets). The microfluidic device is arranged to receive a biological sample and to contain at least one magnetic particle. This microfluidic device may for example comprise a sample inlet, at least one chamber where the magnetic particles are actuated and/or manipulated and/or moved in the sample and a micro fluidic path between the sample inlet and the chamber(s). Additional elements may be provided (e.g. a filter or membrane to separate some biological elements from the biological sample upstream the chamber). The magnetic particles may be contained in the chamber(s), in the microfluidic path or added in the sample before latter is received by the microfluidic device. The microfluidic device further comprises storing means for storing information including a magnetic protocol information in a form readable by the processing device, the magnetic supplier being able to generate magnetic forces on the magnetic particle(s) according to this magnetic protocol information read from the storing means. A purpose is clearly to manipulate the magnetic beads according to this stored magnetic protocol information. This magnetic manipulation in a microfluidic device may be used for instance for mixing magnetic particles in or with the biological sample, for flowing magnetic particles according to a specific path in the microfluidic device or for actuating magnetic particles in view of a bonding with a sensing surface of a biosensor.

The magnetic protocol used for the manipulation of the magnetic beads depends therefore on the magnetic protocol information contained in the microfluidic device: the process for manipulating the magnetic particles is at least partly defined accordingly when the magnetic protocol information is stored in the cartridge. In particular, this information can take into account the method, parameters and conditions of manufacturing the cartridge and the optional assay/reagent contained in it. Furthermore, this magnetic protocol information might also be defined as being able to change the magnetic protocol according to a temperature measured when the magnetic manipulation takes place. This magnetic protocol information may also define a plurality of magnetic protocols associated with condition(s) of use, and one of them being selectable by the processing means if the corresponding condition(s) is fulfilled. This condition(s) might be, without any restriction, a measured temperature, a measured wetting, electronic configuration or accuracy of the processing means contained in the processing device.

The sensitivity and/or accuracy of the magnetic manipulation can therefore be improved.

This magnetic manipulation in a micro fluidic device may be used for instance for mixing magnetic particles in the biological sample, for flowing magnetic particles according to a specific path in the microfluidic device and/or for actuating magnetic particles in view of a bonding with a sensing surface of the microfluidic device.

Optionally, the microfluidic device comprises a chamber having a sensing surface including capturing particles for specifically capturing the magnetic particle(s) and/or analytes included in the biological sample, wherein the magnetic particle(s) is (are) arranged to specifically bind with the analyte(s). And the microfluidic device is arranged so that the presence of bound magnetic beads bound to the sensing surface can be detected by a detector provided in the processing device. In this case, the overall system (microfluidic device+ processing device) is a biosensor.

In a preferred embodiment, the magnetic protocol is a magnetic actuation protocol information, and is included together with calibration information. Calibration information may be used to calibrate and extract the estimated number of magnetic particles from a detection signal received by the detector.

Alternatively or in combination with the aforementioned feature, the chamber of the microfluidic device may comprise the at least one magnetic particle attached therein in a dry state so as to be dispersed in the biological sample when latter is received in the chamber.

Optionally the microfluidic device is arranged to be introduced and held at least partly in the processing device so that the magnetic particle(s) is (are) located proximate the magnetic supplier.

Optionally the micro fluidic device may be made of one single part, the storing means being directly integrated in or on the microfluidic device which is arranged such that, once used with the processing device, the processing device is able to read said information from the storing means. Alternatively, the microfluidic device is made of two parts, the first part being arranged to receive the biological sample and to contain the magnetic particle(s); and the second part comprising a chip comprising the storing means, the chip being arranged such that, once placed proximate the processing device or in the processing device at an appropriate location, the processing device is able to read automatically said information from the storing means.

Optionally said information is provided in the form of an RFID information, a bar code, a 2D bar code, a solid state electronic storage device such as a flash memory, an integrated circuit card, or any combination thereof.

Optionally the micro fluidic device comprises a RFID tag storing said information and a RF emitter to send the information to the processing device. This RFID tag may be a read/write tag. The RFID tag may be a passive tag or an active tag.

Optionally said information contains one or more of the following: frequency, amplitude, duty cycle, polarity and/or status of each generating means; position of the generating means relative to the microfluidic device; number of repetition cycles of the magnetic forces; combination, type and/or duration of magnetic sequence involved in the protocol; the position of each magnetic supplier.

This invention relates also to a processing device arranged to manipulate magnetic particles in a biological sample received in the chamber of a microfluidic device, comprising:

- a magnetic supplier to generate at least one magnetic field according to at least one magnetic protocol so as to manipulate the magnetic particles,
- a reader arranged to read information, including a magnetic protocol information, from storing means comprised in the microfluidic device,
- a processor arranged with the reader and with the magnetic supplier to control the magnetic supplier according to the read magnetic protocol information.

Optionally the reader may comprise a RF receiver to receive the information in a RF form the microfluidic device. The processing device may also comprise a RF emitter to send RFID data to the microfluidic device.

Alternatively to or in combination with the aforementioned paragraph, the reader comprises an optical reader to read a bar code in the storing means of the micro fluidic device.

The invention may also relate to a system for manipulating magnetic particles comprising:

- a processing device comprising a magnetic supplier to generate at least one magnetic field according to at least one magnetic protocol,
- a microfluidic device to be used with the processing device, arranged to receive a biological sample and to contain at least one magnetic particle which can be magnetically manipulated by the magnetic supplier, wherein the microfluidic device comprises storing means for storing information including a magnetic protocol information in a form readable by the processing device, and wherein the processing device comprises a reader able to read the magnetic protocol information from the storing means when the microfluidic device is used with the processing device, and a processor arranged with the reader and with the magnetic supplier so as to control the magnetic supplier according to the read magnetic protocol information.

A particular embodiment of the invention is a biosensor which comprises a cartridge assembly (or microfluidic device) to be used with a sensor (or processing device) for detecting analytes in a biological sample, comprising a cartridge which:

- is arranged to comprise magnetic particles able to bond with at least one type of analyte to be detected, and
- comprises a sensing surface processed or to be processed to include capturing means for capturing the magnetic particles and/or the analytes in view of the detection of the analytes by the sensor;

wherein the sensor comprises generating means for generating magnetic forces according to a magnetic protocol so as to manipulate the magnetic particles, wherein the cartridge assembly comprises storing means for storing information corresponding to the magnetic protocol in a form readable by the sensor.

According to another aspect of said particular embodiment, there is provided a method of manipulating magnetic particles in a sensor, the method comprising the following steps:

a) providing said cartridge assembly, comprising magnetic particles;
b) providing a sensor comprising generating means for generating magnetic forces according to a magnetic protocol so as to perform a corresponding magnetic manipulation of the magnetic particles;
c) placing at least a part of the cartridge of the cartridge assembly into a sensor;
d) reading information regarding the magnetic protocol from the storing means; and
e) performing the magnetic manipulation according to the readout information.

Preferably, the information is read wirelessly and/or optically and/or electronically.

The readout may be performed, e.g., via RFID, Bluetooth, Wi-Fi, IR, bar code, laser, or any combination thereof. Any other known technique to transmit information wirelessly may be used. In particular, any optical, acoustic or electromagnetic transmission of the information is possible.

The information regarding the magnetic actuation protocol may be provided on a chip of the cartridge assembly separate from the cartridge, which comes together with the cartridge (e.g. sold in a same package).

According to a further aspect of said particular embodiment, a sensor is provided with:
- generating means for generating magnetic forces according to a magnetic protocol so as to manipulate magnetic particles embedded in a cartridge assembly,
- a reader adapted to read information regarding a specific magnetic actuation protocol provided in the cartridge assembly. The reader may be any reader which is suitable to read an RFID tag, a barcode, a 2-D barcode, an infrared transmitter and/or a Bluetooth device. It is in particular preferred that the reader is adapted to read differently provided information.

The overall biosensor (i.e. said cartridge assembly and said sensor) may be used to perform either of the above methods. In particular, the biosensor is preferably adapted to automatically detect whether the information is provided on a cartridge or a chip and in which format and to perform a readout in accordance with the result of said detection. Should neither the cartridge nor a chip provide the necessary information regarding the actuation protocol, the biosensor refuses to perform the protocol. Accordingly, the solution in which the information is provided on the cartridge has the advantage over the chip that if the chip is not available (e.g., lost or misplaced), the test can still be performed. Furthermore, the added step of including the chip with each test run can be neglected. In general, each reduction in step number and complexity improves the reliability and ease-of-use of the test.

In general, the actuation protocol is often the same for a whole batch of cartridges. Accordingly, it may also be possible to provide one chip only together with a batch of cartridges.

The present invention is thus also directed to a method for performing a magnetic manipulation of magnetic particles in a sensor, the method comprising the following steps:
a) providing a cartridge assembly that comprises:
   a batch of cartridges, each cartridge comprises:
      magnetic particles able to bond with at least one type of analyte to be detected, and
      a sensing surface processed or to be processed to include capturing means for capturing the magnetic particles and/or the analytes in view of the detection of the analytes by the sensor;
      an identification reference;
   a chip corresponding to said batch, the chip comprising the storing means for storing information corresponding to a magnetic protocol in a form readable by the sensor and optionally a batch reference identifying the batch;
b) providing a sensor able to receive at least a part of a cartridge within and comprising generating means for generating magnetic forces according to a magnetic protocol so as to perform a corresponding magnetic manipulation of the magnetic particles;
c) reading information regarding the magnetic protocol and the optional batch reference from the chip;
d) storing the magnetic protocol and the optional batch;
e) placing at least a part of a cartridge of said batch in the sensor;
f) reading the corresponding identification reference from the cartridge;
g) storing the information regarding the identification number; and
h) performing the magnetic manipulation according to the read-out identification number.

In other words, the information regarding the magnetic actuation protocol is only provided once on a chip which corresponds to a batch of cartridges. The information is then stored on the biosensor. Together with the information regarding the protocol, an identification number is stored which is indicative of the corresponding batch of cartridges. Thus, whenever a cartridge of a specific batch is introduced into the biosensor, the batch can be identified via an identification number provided on the cartridge. The biosensor now simply matches the identification number provided on the cartridge with the identification number stored together with the information regarding the actuation protocol. Then, the biosensor can choose the correct or corresponding protocol and perform the magnetic actuation protocol which is suitable for the cartridge belonging to the specific batch.

As already mentioned above, the information regarding the magnetic actuation protocol preferably contains one or more of the following: frequency, amplitude, duty cycle, polarity and/or status of each generating means (e.g. magnet); number of repetition cycles; combination, type and/or duration of sequence. Preferably, the information is read wireless and/or optically and/or electronically from the chip. It is furthermore preferred that the identification number provided on the cartridge is read wireless and/or optically and/or electronically as well.

It is also conceivable that the number of cartridges per batch is stored together with the identification number. Thus, once the last cartridge of a batch has been used, the information regarding the actuation protocol corresponding to said batch may be deleted from the storage means of the biosensor.

The present invention provides several advantages over the prior art. An important advantage is the ability to customize the actuation protocol for each test and each lot of cartridges produced. An additional crucial advantage is the reduction in possibilities to obtain an erroneous result. The user does not need to pay attention to the specific test type and its features. All he needs to do is to insert the test into the reader. The reader scans for the actuation protocol information on the cartridge and/or chip and performs the correct assay test method. Such techniques are important if the product is intended for approval by, e.g., the regulation body CLIA for use by non-technical users.

The sensor of the biosensor of the present invention can be any suitable sensor to detect the presence of magnetic particles and/or analytes on or near to a sensor surface, based on any property of the particles, e.g. it can detect via magnetic methods (e.g. magnetoresistive, Hall, coils), optical methods (e.g. imaging, fluorescence, chemiluminescence, absorption, scattering, evanescent field techniques, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), combinations thereof, etc. One particularly preferred sensor is based on the technique of frustrated total internal reflection (FTIR) or the giant magnetoresistance (GMR) detection.

DETAILED DESCRIPTION OF AN EMBODIMENT OF THE INVENTION

Figure 1:
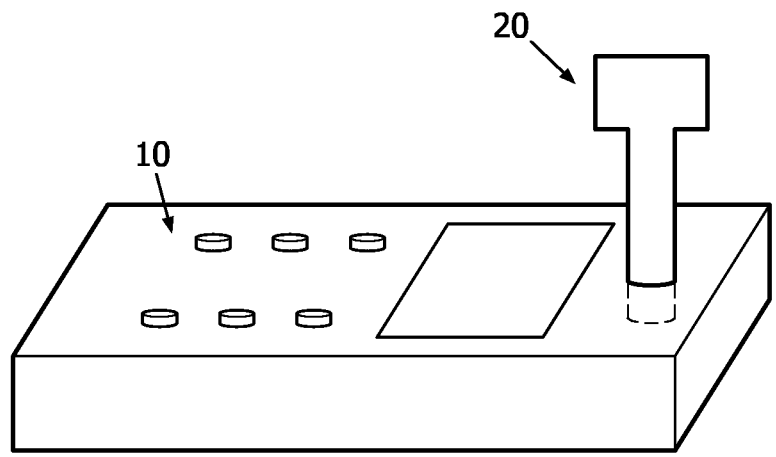
FIG. 1 is a perspective view of a biosensor.

FIG. 1 depicts schematically a biosensor comprises a sensor 10 and a cartridge 20 introduced in the sensor 10.

Figure 2:
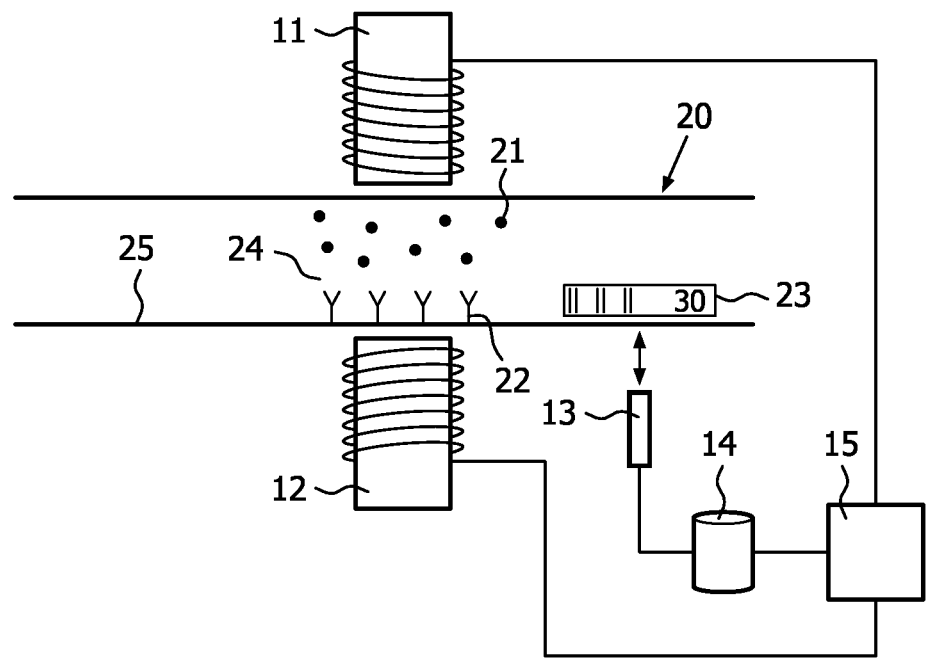
FIG. 2 is a schematic longitudinal cross-section view of the biosensor of FIG. 1.

FIG. 2 depicts schematically the biosensor.

The cartridge 20 comprises means for receiving a biological sample (e.g. urina, saliva or blood) and flow it via a fluidic path (e.g. by capillarity channels or through lateral flow) to a detection location 24 (or chamber 24). Magnetic particles (e.g. each magnetic particle being a superparamagnetic elements embedded in a polymer material, e.g. attached to the detection location or chamber or in the fluidic path in a dry state) are mixed with or dispersed in the sample in the fluidic path or in the detection location 24. These magnetic particles are provided with binding means (e.g. antibodies, antigens, ligand) arranged for specifically binding to at least one type of analyte to detect. The detection location 24 is further provided with a sensing surface 25 comprising capturing means 22 arranged for capturing analytes (sandwich assay configuration) or the magnetic particles non bound to an analyte (competitive assay configuration).

The cartridge 20 further comprises storing means 23 for storing information comprising a magnetic protocol. This storing means 23 may be any kind of storing means able to store any kind of magnetic protocol 30 and able to be read by the sensor 10. This storing means may be one of the aforementioned storing means (e.g. RFID tag, a bar code, a 2D bar code, a solid state electronic storage device such as a flash memory, an integrated circuit card, or any combination thereof). Alternatively, this storing means 23 may be embedded in a chip separate from the cartridge 20 and be part of a cartridge assembly (e.g. the cartridge 20 and the storing means are sold in a same package); in this case, the chip can operate when located proximate the sensor 10 or when inserted in a dedicated place in the sensor 10. The magnetic protocol may be stored in the storing means 23 during or after the manufacturing of the cartridge 20, taking into account of the specificities of the components embedded in the cartridge 20, the conditions of manufacturing and of measurement performed on the cartridge or other parameters.

The sensor 10 comprises a certain number (e.g. two, three or four) of electromagnets 11-12 arranged on either side or on both sides of the detection location 24 of the cartridge 20, to apply magnetic forces to the magnetic particles 21 in order to manipulate them. Manipulation may comprise different steps; e.g.: applying no magnetic forces to allow magnetic particles to bind with the analytes in the sample; applying magnetic forces in order to attract the magnetic particles towards the sensing surface 25; a magnetic wash to repulse the magnetic particles not binding to the sensing surface 25 from the sensing surface 25; applying no magnetic forces to allow the detection.

The sensor 10 is also provided with a reader 13 able to read the magnetic protocol from the storing means 23, storing means 14 (e.g. an electronic memory) to store the magnetic protocol, processing means 15 (e.g. a controller, a processor) to command the electromagnets 11-12 according to the stored magnetic protocol. Therefore the magnetic protocol is specifically tailored with respect to the type cartridge 20 used, without the need for a user or a technical expert to act or amend the magnetic protocol stored in the sensor 10.

The sensor 10 is preferably provided with detecting means (e.g. for optical detection, such as for example FTIR or fluorescence detection, or magnetic detection, using e.g. the GMR technique), using well-known techniques.

The storing means 23 may further store some calibration data used to calibrate the signal detected by the detecting means, in order to retrieve the information on the analytes (e.g. amount of analytes bound to the sensing surface 25).

In a particular embodiment, the cartridge 10 is part of a batch of cartridges, and the storing means 23 stores also a reference to identify the cartridge. Alternatively, in the case the storing means 23 is in a chip separate from the cartridge 20 (as aforementioned), this storing means can also store a reference identifying the batch, and each cartridge may be provided with a second storing means for storing a reference to identify it. Further to the reader 23, the sensor 10 may be provided with a second reader (not shown) to detect the reference of the cartridge 20 or, alternatively, the same reader 13 is used both for detecting the reference of the cartridge and the information contained in the storing means 23 of the chip.

While the invention has been illustrated and described in detail in the foregoing description, such description is to be considered illustrative or exemplary and not restrictive; the invention is not limited to the disclosed embodiments. In particular, this invention encompasses also other biosensing assays in which the magnetic particle is not used as a label but as a carrier for the manipulation of biological molecules (e.g. molecule extraction, transport, up-concentration, purification, and the like). Examples can be found in nucleic acid detection/assays. Here precise magnetic particle motion is also required and a cartridge containing the actuation protocol is advantageous.

Other variations to the disclosed embodiments can be understood and effected by those skilled in the art in practicing the claimed invention, from a study of the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A microfluidic device for performing a magnetic particle assay, the microfluidic device comprising:
    a chamber configured to receive magnetic particles and a biological sample for mixing with the magnetic particles;
    an identifier including information for identifying a magnetic actuation protocol associated with the microfluidic device and conditions of manufacturing of the microfluidic device;
    a magnetic supplier configured to generate magnetic forces;
    a reader configured to read the information from the identifier; and
    a processing device including a processor, a reader and a magnetic supplier,
    wherein the reader is configured to read the information from the identifier, the magnetic supplier is configured to generate magnetic forces, and the processor is configured to control the magnetic supplier for generation of magnetic forces on the magnetic particles according to the magnetic actuation protocol identified by the information read from the identifier.

2. The microfluidic device according to claim 1, wherein the chamber comprises a sensing surface for capturing at least one the magnetic particles and analytes included in the biological sample, wherein the magnetic particles are arranged to specifically bind with the analytes, and wherein the processing device further comprises a detector configured to detect presence of bound magnetic beads bound to the sensing surface.

3. The microfluidic device according to claim 1, wherein the magnetic particles are attached in the chamber in a dry state so as to be dispersed in the biological sample when the biological sample is received in the chamber.

4. The microfluidic device of claim 1, wherein the chamber is located proximate the magnetic supplier.

5. The microfluidic device according to claim 1, wherein the identifier comprises a chip, and when the chamber is placed proximate to or in the processing device, the processing device is configured to automatically read said information from the identifier.

6. The microfluidic device according to claim 1, wherein the information is in a form selected from at least one of a Radio-Frequency Identification (RFID), a bar code, a 2D bar code, a solid state electronic storage device, an integrated circuit card, and any combination thereof.

7. The microfluidic device according to claim 1, wherein the identifier comprises a Radio-Frequency Identification (RFID) tag and further comprising an RF emitter configured to send the information to the processing device.

8. The microfluidic device according to claim 7, wherein the RFID tag is a read/write tag.

9. The microfluidic device according to claim 7, wherein the RFID tag is a passive or active tag.

10. The microfluidic device according to claim 1, further comprising at least one magnets, wherein the information further includes at least one of:
at least one frequency, amplitude, duty cycle, polarity and status of each magnet;
position of the magnetic supplier relative to the microfluidic device;
number of repetition cycles of the magnetic forces; and
at least one combination, type and duration of magnetic sequence.

11. A processing device configured to manipulate magnetic particles in a biological sample, the processing device comprising:
a microfluidic device for performing a magnetic particle assay and having
a chamber including magnetic particles and a biological sample for mixing with the magnetic particles, and
an identifier including information for identifying a magnetic protocol associated with the microfluidic device and conditions of manufacturing of the microfluidic device;
a magnetic supplier configured to generate at least one magnetic field according to at least one of a plurality of magnetic protocols so as to manipulate the magnetic particles;
a reader configured to read the identifier when the microfluidic device is within a predetermined distance from the reader; and
a processor configured to control the magnetic supplier according to the magnetic protocol.

12. The processing device according to claim 11, wherein the reader comprises a receiver to receive the information in a Radio-Frequency (RF) form from the microfluidic device.

13. The processing device of claim 12, further comprising an RF emitter to send Radio-Frequency Identification (RFID) to the microfluidic device.

14. The processing device according to claim 11, wherein the information comprises a bar code and the reader comprises an optical bar code reader.

15. A system for manipulating magnetic particles when performing a magnetic particle assay, the system comprising:
a processing device comprising a processor, a reader, and a magnetic supplier configured to generate at least one magnetic field according to at least one of a plurality of magnetic protocols identified by information read by the reader; and
a microfluidic device having
a chamber having one of a plurality of combinations of magnetic particles and a biological sample for mixing with the magnetic particles,
an identifier for identifying a protocol associated with the microfluidic device and conditions of manufacturing type of the microfluidic device, and
a reader configured to read the conditions of manufacturing of the microfluidic device,
wherein the processor is configured to control the magnetic supplier according to the magnetic protocol identified by the information read by the reader.

16. The microfluidic device of claim 1, wherein the microfluidic device is manufactured in batches and the magnetic actuation protocol is customized for each batch of microfluidic devices, wherein the conditions of manufacturing include a number of microfluidic devices per batch, and wherein the processing device is further configured to delete information regarding the magnetic actuation protocol corresponding to the batch once a last microfluidic device of the batch has been used.

17. The microfluidic device of claim 1, wherein the processor is further configured to change the magnetic actuation protocol according to a temperature measured when magnetic manipulation takes place.

18. The microfluidic device of claim 1, wherein the information take into account a reagent contained in the microfluidic device, and wherein the processor is further configured to select among magnetic actuation protocols of the identifier based on a fulfilled condition related to one of a measured temperature and a measured wetting of the microfluidic device.

19. The processing device of claim 11, wherein the information take into account a reagent contained in the microfluidic device, wherein the microfluidic device is manufactured in batches and the magnetic actuation protocol is customized for each batch of microfluidic devices, wherein the conditions of manufacturing include a number of microfluidic devices per batch, wherein the processor is further configured to delete information regarding the magnetic actuation protocol corresponding to the batch once a last microfluidic device of the batch has been used, wherein the processor is further configured to change the magnetic actuation protocol according to a temperature measured when magnetic manipulation takes place, and wherein the processor is further configured to select among magnetic actuation protocols of the identifier based on a fulfilled condition related to one of a measured temperature and a measured wetting of the microfluidic device.

20. The system of claim 15, wherein the information take into account a reagent contained in the microfluidic device, wherein the microfluidic device is manufactured in batches and the magnetic actuation protocol is customized for each batch of microfluidic devices, wherein the conditions of manufacturing include a number of microfluidic devices per batch, wherein the processor is further configured to delete information regarding the magnetic actuation protocol corresponding to the batch once a last microfluidic device of the batch has been used, wherein the processor is further configured to change the magnetic actuation protocol according to a temperature measured when magnetic manipulation takes place, and wherein the processor is further configured to select among magnetic actuation protocols of the identifier based on a fulfilled condition related to one of a measured temperature and a measured wetting of the microfluidic device.

\* \* \* \* \*